United States Patent [19]

Buchan

[11] 4,192,763

[45] Mar. 11, 1980

[54] CHLORINE TABLET AND THE PREPARATION THEREOF

[76] Inventor: Pieter W. W. Buchan, 2 Nicolyn Ave., Ruiterhof, Randburg, South Africa

[21] Appl. No.: 874,864

[22] Filed: Feb. 3, 1978

[30] Foreign Application Priority Data

Feb. 16, 1977 [ZA] South Africa .................. 77/0938

[51] Int. Cl.$^2$ .................. C11D 3/48; C01B 11/06; C02B 1/18
[52] U.S. Cl. .................. 252/187 H; 252/90; 252/106; 252/176; 423/474; 424/149
[58] Field of Search .................. 252/187 H, 90, 106, 252/176; 423/163, 431, 474; 424/14, 149

[56] References Cited

U.S. PATENT DOCUMENTS

| | | | |
|---|---|---|---|
| 1,765,013 | 6/1930 | Hershman | 252/187 H |
| 1,787,048 | 12/1930 | MacMullin et al. | 252/187 H |
| 2,023,459 | 12/1935 | Bachman | |
| 2,590,794 | 3/1952 | Robson | 252/187 H |
| 3,251,647 | 5/1966 | Nicolaison | 252/187 H |
| 3,584,996 | 6/1971 | Hughes | 252/187 H |
| 3,669,894 | 6/1972 | Faust | 252/187 H |
| 3,793,216 | 2/1974 | Dychdala | 252/187 H |
| 3,872,219 | 3/1975 | Sakowski | 423/474 |
| 4,035,484 | 7/1977 | Faust et al. | 423/474 |
| 4,105,565 | 8/1978 | Wojtowicz | 252/187 H |

OTHER PUBLICATIONS

Condensed Chemical Dictionary, 8th Edition, Van Nostrand 1974, pp. 537 & 953.

*Primary Examiner*—Richard D. Lovering
*Assistant Examiner*—Irwin Gluck
*Attorney, Agent, or Firm*—Dressler, Goldsmith, Clement, Gordon & Shore, Ltd.

[57] ABSTRACT

A method of forming a chlorine tablet for combatting bacterial and algaecidal contamination of swimming pools and the like, which includes the step of pressing a mixture of calcium hypochlorite and chloride of lime, together with a minor proportion of zinc stearate as a tabletting lubricant, into a tablet. The invention further relates to such a tablet.

13 Claims, No Drawings

CHLORINE TABLET AND THE PREPARATION THEREOF

This invention relates to a chlorine tablet and to the preparation thereof. More particularly, this invention relates to a chlorine tablet which constitutes a source of available chlorine for disinfecting and sanitizing.

In accordance with the invention, a method of forming a chlorine tablet, includes the step of pressing a mixture of calcium hypochlorite and chloride of lime into a tablet.

The proportion by weight of chloride of lime may conveniently be less than about 20%.

In an embodiment of the invention, the proportion by weight of chloride of lime may be between about 5% and about 15%.

In an example of the invention, the proportion by weight of chloride of lime may be about 10%.

From experiments conducted by applicant, it has been found that as the proportion by weight of chloride of lime is increased, the rate of dissolution of a chlorine tablet in water decreases, the alkalinity increases and the level of insolubles increases.

The proportion by weight of chloride of lime may therefore be controlled for the intended use of the tablet, to balance the required rate of dissolution against the level of insolubles which can be tolerated and, to a lesser extent, the degree of alkalinity which can be tolerated.

Since the percentage of available chlorine is less in chloride of lime than in calcium hypochlorite, the percentage of available chlorine will decrease as the proportion by weight of chloride of lime increases. This is therefore a further factor which should be considered when the proportion by weight of chloride of lime which should be used in a particular instance, is selected.

Insofar as applicant has been able to establish, the exact constitution of chloride of lime has not yet been finally determined.

However, chloride of lime is the product formed by passing chlorine over dry slaked-lime, and it is believed to comprise a mixture or complex of calcium hypochlorite, calcium hydroxide and a non-hygroscopic form of calcium chloride.

Theoretically chloride of lime has an available chlorine percentage of about 32% by weight.

The calcium hypochlorite may conveniently comprise a commercial granular calcium hypochlorite preparation.

Commercially available granular calcium hypochlorite preparations generally contain at least about 50 to 60% and preferably about 70% by weight of calcium hypochlorite.

These commercial preparations generally have an available chlorine percentage of about 70%.

In an embodiment of the invention, the calcium hypochlorite may be in the form of a high test calcium hypochlorite composition having a calcium hypochlorite content of at least about 80%.

The method of this invention may include the step of incorporating a minor proportion of a suitable metal salt of a suitable fatty acid as a tabletting lubricant for the tabletting of the mixture.

The fatty acid may conveniently be a fatty acid having at least 10 carbon atoms.

The metal may be any metal which is compatible with calcium hypochlorite, such as zinc, magnesium, or the like.

In an embodiment of the invention, the tabletting lubricant may comprise a metal salt of stearic acid such as, for example, zinc or magnesium stearate.

The proportion by weight of tabletting lubricant incorporated in the mixture may be any convenient proportion which will facilitate appropriate tabletting of the mixture.

Thus, for example, the proportion by weight of tabletting lubricant may be between about 0.5% and about 3%, or more.

In an embodiment of the invention, the proportion by weight of tabletting lubricant in the form of zinc stearate, may be in the region of about 0.5 and 2%.

In a specific example of the invention, the proportion by weight of zinc stearate may be about 1%.

The invention further extends to a chlorine tablet whenever formed by the method as described herein.

The invention further extends to a chlorine tablet comprising a compressed mixture of calcium hypochlorite and chloride of lime.

The proportion by weight of chloride of lime may be less than about 20%, and conveniently between about 5 and about 15%.

In an embodiment of the invention, the proportion by weight of chloride of lime may be about 10%.

The tablet may include a minor proportion of a metal salt of a suitable fatty acid as a tabletting lubricant.

The tabletting lubricant may be as hereinbefore described, and in the proportions as hereinbefore specified.

In forming a tablet in accordance with this invention, at least one of the components of the mixture may be in granular form or have a sufficient granular content so that effective tabletting can be achieved. The other component or the balance, as the case may be, may be in the form of a light or heavy powder.

In an embodiment of the invention, the calcium hypochlorite may conveniently be in granular form, with the chloride of lime in powder form to provide for effective tabletting of the mixture by conventional tabletting means.

Tablets in accordance with this invention may be provided in any desired size depending upon intended use of the tablets.

Typically, for use in the disinfecting and sanitizing of swimming pools and bodies of water, tablets having masses of between about 50 and 100 grams, between about 150 and about 200 grams, and larger in certain instances, may conveniently be provided.

The invention is illustrated by way of example, with reference to the following examples.

EXAMPLE 1

A series of experiments were conducted in which four different mixtures were formed comprising differing percentages of commercially available calcium hypochlorite granules, chloride of lime, and zinc stearate. These different mixtures were compressed in standard tabletting apparatus to form tablets having a mass of about 195 grams and a diameter of about 70 mm. Similar tablets were, for the purposes of comparison formed out of calcium hypochlorite granules alone, and out of calcium hypochlorite granules and zinc stearate.

Six different sets of tablets were thus formed. In each of the experiments which was conducted, the six different tablets were placed in separate floating baskets in a vessel containing 9,000 l of water at a temperature between 25° to 27° C.

The water was recycled at a rate of 900 l per hour.

The average of the experimental results which give the average dissolution rates of the various tablets, are set out in Table I below.

TABLE I.

| Tablet No. | *Calcium hypochlorite | *Chloride of Lime. | *Zinc Stearate. | Dissolving time Hours. |
|---|---|---|---|---|
| 1 | 94 | 5 | 1 | 130 |
| 2 | 89 | 10 | 1 | 164 |
| 3 | 84 | 15 | 1 | 182 |
| 4 | 79 | 20 | 1 | 196 |
| 5 | 100 | 0 | 0 | 12 |
| 6 | 99 | 0 | 1 | 125 |

*All percentages by weight.

It will be noted from Table I above that the rate of dissolution of the calcium hypochlorite tablet (No. 5), is very rapid—about 12 hours. When zinc stearate is included as a tabletting lubricant (Table No. 6), it not only facilitates tabletting but provides the additional advantage in that it substantially reduces the rate of dissolution of the calcium hypochlorite tablet.

It will be noted in particular however that as the proportion by weight of chloride of lime is increased, the rate of dissolution of the tablet decreases.

EXAMPLE 2

A further series of experiments were conducted in which a comparison was made between tablets which included chloride of lime and tablets which did not to compare the rates of dissolution and, in addition, the rate of release of chlorine.

In conducting these experiments, tablets having a mass of about 63 g with a diameter of about 40 mm where prepared from 10% by weight of chloride of lime, 1% by weight of zinc stearate, and the balance commercial granular calcium hypochlorite.

These tablets in accordance with this invention were estimated to have an available chlorine percentage of about 66%.

In the experiments which were conducted, a tablet was placed in a floating basket in a vessel containing 9,000 l of water at a temperature range of between about 24 and 28° C.

The water was circulated at the rate of 900 l per hour.

The water was exposed to the elements and was stabilized with 30 parts per million of isocyanuric acid.

The average of the results of these experiments conducted with the tablets in accordance with this invention, are set out in Table II below.

Comparative experiments were then conducted with tablets which were prepared from commercial granular calcium hypochlorite and 1% zinc stearate to provide tablets having a mass of about 57 g and a diameter of about 40 mm.

These comparative tablets were estimated to have an available chlorine percentage of about 69%.

The experiments on the comparative tablets were conducted in exactly the same way as the experiments on the tablets in accordance with this invention and the average results of these experiments are set out in Table III below.

TABLE II

Tablets comprising 89% Calcium Hypochlorite, 1% Zinc Stearate and 10% Chloride of Lime.

| Hours. | parts per million available chlorine. |
|---|---|
| 0 | 0 |
| 24 | 7 |
| 48 | 4 |
| 72 | 4 |
| 96 | 2,8 |
| 120 | 1,4 |

TABLE III

Tablets comprising 99% Calcium Hypochlorite, 1% Zinc Stearate.

| Hours. | parts per million available chlorine. |
|---|---|
| 0 | 0 |
| 24 | 6 |
| 48 | 6 |
| 72 | 2,4 |
| 96 | 1,8 |
| 105 | 0,75 |

From the experiments which were conducted, it was found that the tablets in accordance with this invention dissolved in about 36 hours, whereas the comparative tablets dissolved in about 20 hours.

It will be noted from the average experimental results as set out in Tables II and III, that in both cases a residual level of chlorine was maintained for some time after the tablets had dissolved.

However, in the case of the tablets in accordance with this invention, the residual level of chlorine tailed off more slowly than in the case of the comparative tablets which did not include chloride of lime.

Without wishing to be bound by theory, applicant believes that the relatively slower tailing off of the residual level of chlorine in the case of the tablets in accordance with this invention, is attributable to the fact that the calcium hypochlorite dissociates fairly rapidly to provide the initial high level of chlorine in the water, whereafter the relatively insoluble chloride of lime will release chlorine to maintain an effective residual chlorine level for a reasonable time thereafter.

In the case of the comparative tablets which do not include chloride of lime, the zinc stearate has the effect of reducing the rate of dissolution of the calcium hypochlorite. However, the calcium hypochlorite nevertheless dissolves fairly rapidly to provide an initial high level of chlorine, whereafter the chlorine level tails off relatively rapidly.

It should be noted that the tablets in accordance with this invention of which the average results are set out in Table II above, had a mass of only 63 grams.

By making these tablets of a mass which is conventional for tablets for use in domestic swimming pools and the like, namely about 200 grams, the tablets would dissolve over a period of about four to six days. In accordance with applicant's experience, this is an adequate period for this type of application, bearing in mind that the average results in Table II above indicate that there will be a sufficiently high residual level of chlorine after complete dissolution, for effective disinfecting and sanitation of water.

As far as applicant has been able to establish, under normal circumstances, a residual chlorine level of between about 0.5 to 1 parts per million is normally sufficient for prompt destruction of bacterial and algaecidal contamination of swimming pools.

Where organic matter is contained in the swimming pool or nitrogenous compounds have been introduced as a result of rain, temporary chlorine level boosts are usually required to ensure that there will be sufficient residual chlorine to combat normal bacterial and algaecidal contamination.

It is therefore an advantage of the embodiment of the invention as illustrated with reference to the Examples, that a chlorine tablet is provided wherein the rate of dissolution of calcium hypochlorite has been retarded sufficiently to allow the tablet to be used effectively for combatting bacterial and algaecidal contamination of bodies of water, swimming pools, and the like.

It is a further advantage that the tablet can provide an initial chlorine level peak which is followed by a gradual tailing off which will maintain a sufficient residual chlorine level for a reasonable period.

It is a further advantage of the invention that chloride of lime is compatible with calcium hypochlorite and, since it is in powder form, it mixes readily with commercial granular calcium hydrochlorite and facilitates the formation of tablets.

Where a suitable tabletting lubricant such as zinc stearate is included, the zinc stearate not only facilitates tabletting of the mixture, but assists in reducing the rate of dissolution of calcium hypochlorite.

It is a further advantage that chloride of lime is relatively inexpensive and, in addition to reducing the rate of dissolution of calcium hypochlorite, it has a reasonbly high level of available chlorine, thereby contributing to the chlorine which is available for combatting bacterial and algaecidal contamination.

What is claimed is:

1. A method of forming a chlorine tablet, which includes the step of admixing calcium hypochlorite with chloride of lime and pressing said mixture into a tablet.

2. A method according to claim 1, in which the proportion by weight of chloride of lime is between about 5% and about 15%.

3. A method according to claim 2, in which the proportion by weight of chloride of lime is about 10%.

4. A method according to claim 1 in which the calcium hypochlorite is in the form of a high test calcium hypochlorite composition.

5. A method according to claim 1, in which a minor proportion of a metal salt of a suitable fatty acid is included as a tabletting lubricant.

6. A method according to claim 5, in which the tabletting lubricant comprises zinc stearate.

7. A method according to claim 6, in which the proportion by weight of zinc stearate is about 1%.

8. A chlorine tablet comprising a compressed mixture of calcium hypochlorite and chloride of lime.

9. A tablet according to claim 8, in which the proportion by weight of chloride of lime is between about 5% and about 15%.

10. A tablet according to claim 9, in which the proportion by weight of chloride of lime is about 10%.

11. A tablet according to claim 8, in which the calcium hypochlorite is in the form of a high test calcium hypochlorite composition.

12. A table according to claim 8, in which a minor proportion of a metal salt of a suitable fatty acid was included in the mixture as a tabletting lubricant.

13. A tablet according to claim 12, in which the tabletting lubricant comprises zinc stearate.

* * * * *